United States Patent [19]
Leitz et al.

[11] 4,071,297
[45] Jan. 31, 1978

[54] METHOD AND APPARATUS FOR PHOTOELECTRICALLY DETERMINING THE POSITION OF AT LEAST ONE IMAGE FOCUS PLANE

[75] Inventors: Ludwig Leitz; Knut Heitmann; Eckart Schneider, all of Wetzlar; Klaus Dieter Schaefer, Braunfels, all of Germany

[73] Assignee: Ernst Leitz GmbH, Wetzlar, Germany

[21] Appl. No.: 673,726

[22] Filed: Apr. 5, 1976

Related U.S. Application Data

[63] Continuation-in-part of Ser. No. 479,525, June 14, 1974, abandoned.

[30] Foreign Application Priority Data

June 18, 1973 Germany ............................ 2330940

[51] Int. Cl.² ............................................... G01C 3/08
[52] U.S. Cl. ........................................ 356/4; 356/28; 356/156
[58] Field of Search ................ 356/4, 5, 28, 156, 167, 356/170

[56] References Cited

U.S. PATENT DOCUMENTS

| | | | |
|---|---|---|---|
| 3,546,467 | 12/1970 | Benjamin, Jr. et al. | 356/1 |
| 3,781,110 | 12/1973 | Leitz et al. | 356/4 |

FOREIGN PATENT DOCUMENTS

| | | | |
|---|---|---|---|
| 1,249,302 | 10/1971 | United Kingdom | 356/28 |

*Primary Examiner*—S. C. Buczinski
*Attorney, Agent, or Firm*—Gilbert L. Wells

[57] ABSTRACT

A system for determining photoelectrically the position of at least one focus plane of an image within an optical apparatus, wherein the object is reproduced at least at one spatial frequency filter of an optical image correlator and there is measurement and/or display of the light fluxes leaving the local frequency filter.

In this system light fluxes traversing differing pupil sections of the reproducing optics are modulated in common by a spatial frequency filter and are split up geometrically or physically, or by means of additional modulation in correspondence with the pupil sections. They are consecutively or simultaneously projected on a common photoelectric receiver or on separate photoelectric receivers, the output signals of which are processed further for purposes of controlling display and-/or follow-up devices.

47 Claims, 21 Drawing Figures

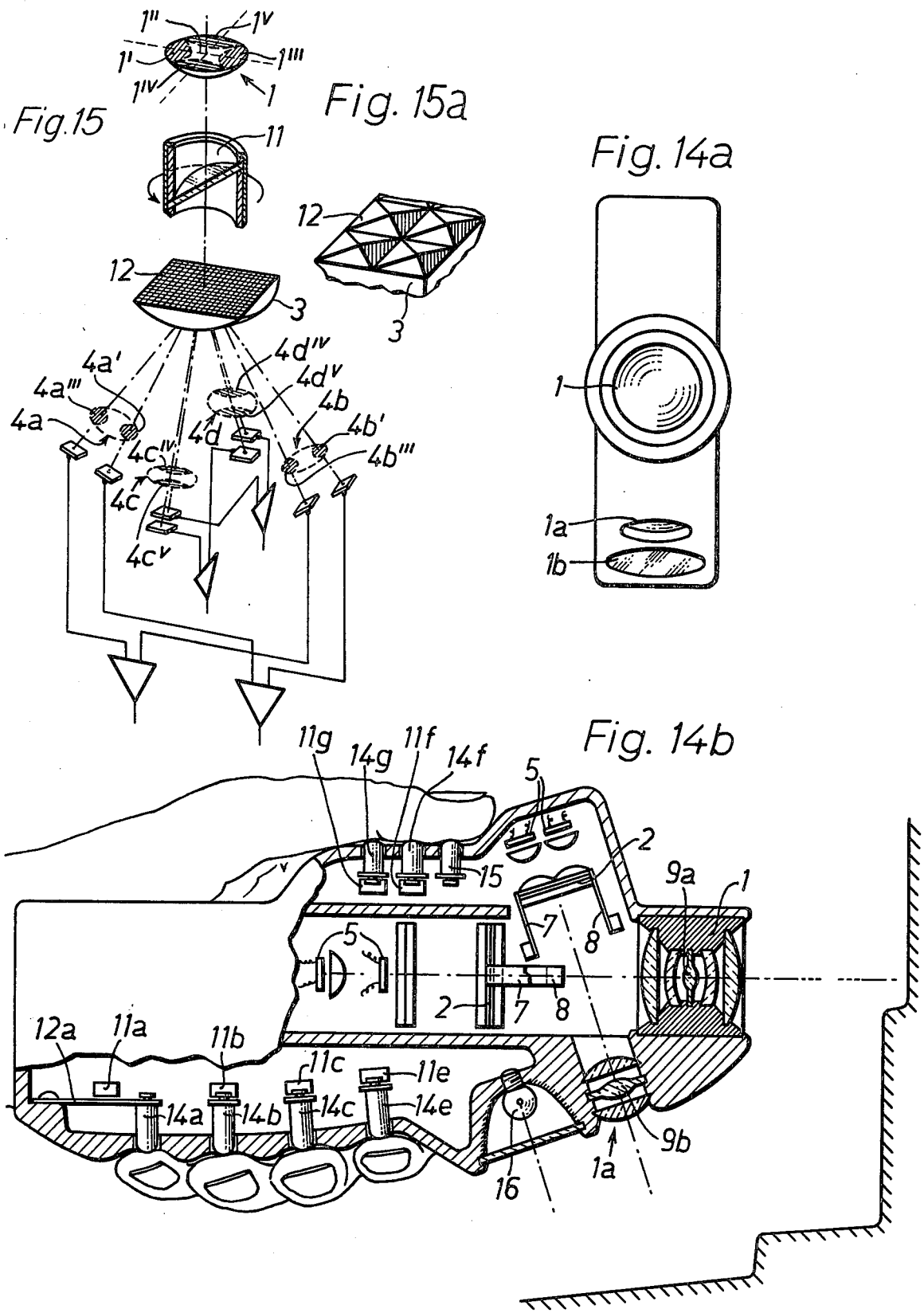

METHOD AND APPARATUS FOR PHOTOELECTRICALLY DETERMINING THE POSITION OF AT LEAST ONE IMAGE FOCUS PLANE

CROSS REFERENCES TO RELATED APPLICATIONS

The present application is a continuation-in-part of application Ser. No. 479,525, filed June 14, 1974 and now abandoned.

Applicants claim priority under 35 U.S.C. 119 for Application P 23 30 940.2, filed June 18, 1973 in the Patent Office of the Federal Republic of Germany. The priority document is contained in the file of Application Ser. No. 479,525.

Assignees copending Application Ser. No. 333,514, filed Feb. 20, 1973, now U.S. Pat. No. 3,856,401 is incorporated herein. FIGS. 15 and 15a of the present application show improvements and further limitations of FIGS. 4 and 4a of U.S. Pat. No. 3,856,401.

BACKGROUND OF THE INVENTION

The invention is particularly related to a method and apparatus for photoelectrically determining the position of at least one focus plane of an image within an optical instrument. The object is reproduced on at least one spatial frequency filter of an optical image correlator and measurement or display of the light fluxes leaving the spatial frequency filter takes place.

The state of the prior art may be ascertained by reference to U.S. Pat. No. 3,781,110 of Leitz et al which issued Dec. 25, 1973, and the references incorporated therein. U.S. Pat. No. 3,781,110 is incorporated herein.

Such methods for photoelectrically determining the focus plane are known. The bundle of light rays from the objective passes through a modulating frequency filter and thereupon is incident upon a photoelectric receiver and the AC output signal thereof is analyzed regarding its amplitude. Furthermore, systems have been proposed, wherein several exit pupils partly overlap one another, or where two exit pupils separately direct light on an associated photoelectric receiver for each. In the first mentioned embodiment, use is made of a single pupil sector when the optical-electronic (optronic) distance measurement is undertaken. In the latter embodiment, use is made summarily of the sector cut-outs on one side, as well as of the symmetrical one on the other of the split-up pupils. These devices do not sufficiently consider the presence of beam centers of gravity between the right and left pupil halves, which though symmetric, nevertheless are different in perspective with respect to the object, that is, there is failure to make full use of ray parallax in the pupils.

SUMMARY OF THE INVENTION

Having in mind the limitations of the prior art, it is an object of the present invention to feed the full informational content of the spatial position of the object being measured contained in the light bundle picked up by the sensor optics to a qualitatively and quantitatively improved analysis system, making use separately of the differing parallactic gravity ranges of the entrance pupil.

The present invention especially relates to the magnitude and sign of the deviation or motion of the object to be measured in three coordinates.

The object of the present invention is achieved in that light fluxes traversing different pupil regions of the reproducing optics are modulated in common by the spatial frequency filter and are split up corresponding to the pupil regions geometrically or physically, or by additional modulation, whereupon they are applied consecutively or simultaneously to a common or to separate photoelectric receivers. The output signals of these receivers are further processed in order to control a display and/or follow-up device. As regards the sign-dependent control of the display and/or control system, use is made of the relative magnitudes of incident electrical signals, and/or in case of a relative motion between the spatial frequency filter and the image of the phases and/or the frequencies.

The system of the present invention is characterized in that the light fluxes traversing the different pupil regions of the optics when a spatial frequency filter system generating push-pull phase light fluxes is being used, are applied, following their being split up into push-pull phase pairs, either consecutively to a common pair of receivers or simultaneously to separate pairs of photoelectric receivers. The output signals from each pair of receivers associated with a given pupil region are applied in known manner to a push-pull amplifier, and the output signals from these amplifiers subsequently are compared with respect to magnitudes for the purpose of the sign-related control of a display or follow-up device, and/or with respect to phase shifts or frequencies in the case of relative motions between spatial frequency filter and image.

BRIEF DESCRIPTION OF THE DRAWINGS

The present invention is described below in further detail by means of the embodiments illustrated in the schematic figures, wherein

FIG. 14a shows a device for orienting blind people;

FIG. 14b shows the device of FIG. 14a in longitudinal section;

FIG. 15 is a device for photoelectrically determining the position of an object in three coordinates;

FIG. 15a is a detailed showing of the grating used in FIG. 15; and

FIG. 16 is a schematic plan view showing an arrangement for photoelectrically determining the position of

DESCRIPTION OF THE PREFERRED EMBODIMENTS

Figure 1:
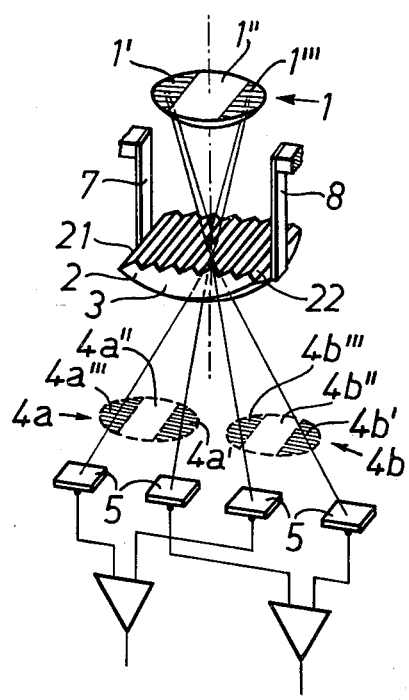
FIG. 1 is a schematic plan view showing an arrangement for photoelectrically determining the position of an image focus plane.

FIG. 1 shows an arrangement with an objective 1 and a spatial frequency filter in the form of a prismatic grating 2. Such a prismatic grating 2 is disclosed in U.S. Pat. No. 2,527,896. The grating 2 is suspended from two piezo-electric elements 7, 8, the former driving the grating to perform motions normal to the direction of the grating grooves, the latter monitoring the grating motion. Piezo-electric element 8 facilitates the use of a self-excited drive circuit (not shown). As shown in the drawing, two sections of the aperture at objective 1 are especially referenced by 1' and 1''', the intermediate part of the objective being denoted by 1''. The boundary edges of regions 1', 1'' and 1''' are laid out so as to be essentially normal to the direction of motion of the grating. Such an objective 1 is disclosed in British Pat. No. 1,249,302.

The optical surface on the other side of the grating 2 is formed as a field lens 3, and in combination with the refracting effect of prismatic grating 2 reproduces the entrance pupil of objective 1 as two separately located pupil images 4a and 4b, each of latter containing aperture section images 4a' through 4a''', and 4b' through 4b''', respectively corresponding to the aperture sections of objective 1. Such pupil images 4a and 4b are disclosed in British Pat. No. 1,249,302. Simultaneously the two side groups of the grating cause image separation, and pupil images 4a and 4b therefore are derived from the light fluxes having traversed different sets of lateral prisms of the grating. The result is complementarity of one pupil image with respect to the other. Because of the motion of prismatic grating 2, these light fluxes will alternate periodically with respect to the pupil images. Thus, the position of the reproduced object structure relative to the flanks or sides 21, 22 of the grating 2 is critical as regards illumination of pupil images 4a or 4b, whereas illumination of pupil image ranges 4a' and 4a''', or 4b' and 4b''' depends critically on the parallax differences (solid angles) for different object regions. It will be noted that the light flux through aperture section 1'' of objective 1 is not utilized. Photoelectric receivers behind pupil images 4a and 4b are designed and arrayed accordingly. Circuit arrangements concerning these receivers and other components such as amplifiers are discussed further below.

Obviously, knowledge of the position of the image focus plane then allows obtaining in known manner the distance between object and objective.

Other devices than the one shown above, i.e., a piezoelectric element for grating 2, may be used, for instance moving coils.

Figure 2:
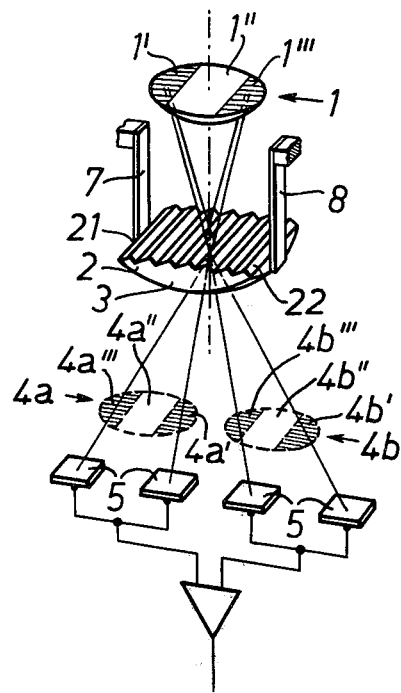
FIG. 2 is a schematic plan view showing an arrangement of FIG. 1 with summing of the pupil parts.

If the sign of the object motion is not needed, the photoelectric receivers 5 associated with the pairs of pupil sections 4a', 4a''', or 4b', 4b''' may be connected pairwise in parallel, as shown in FIG. 2. The two receiver groups deliver push-pull phase signals, a markedly pronounced amplitude maximum being obtained when there is spatial coincidence between image plane and grating.

Figure 3:
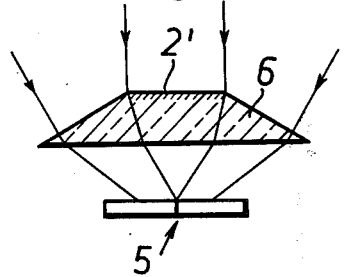
FIG. 3 shows the light being applied to a photoelectric receiver group or set.

If, in lieu of pairs of receivers in parallel, one wishes to provide only one receiver, then care must be taken that the bundles of rays passing through the objective section 1''' do not affect such a photoelectric receiver 5. Due to a stop 2' the light of as high as possible an illumination intensity and lacking any blank or null information will pass from the objective section 1'' through a prism or a refracting cone 6, reaching receiver 5 with full information concerning the ray parallaxes, as shown in FIG. 3.

Figure 4:
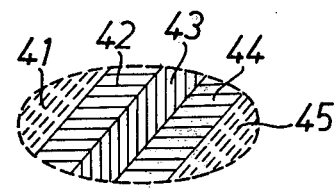
FIG. 4 shows an embodiment of the subdivision of the pupil.

FIG. 4 shows an aperture subdivision for entrance objective 1, which also occurs in the associated pupil images. The total aperture is subdivided into several zone strips 41, 42, 44, 45 for distance measurement and in a strip 43 for motion measurement.

Associated photoelectric receiver groups (not shown) are subdivided correspondingly. Elongated pupil strip 43 is especially suited for measuring object motions transverse to the grating strips of spatial frequency filter grating 2, that is, transverse to longitudinal direction, because it provides maximum image depth of field with respect to the direction of motion. Outer strips 41 and 45 are suited for determining accurately greater object distances and strips 42 and 44 for lesser ones, the spatial separation of the pupil sections represents the measuring basis of the system.

Figure 5:
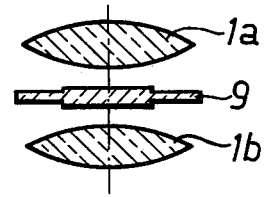
FIG. 5 shows a zone plate arrangement within an objective.

FIG. 5 shows an arrangement of a zone plate of zone lens 9, in cross sectional form, between two lenses 1a and 1b making up an objective. Plate 9 is designed in such manner that for any given pupil zone, which may be for instance annular or strip-like, objects a given distance away may be reproduced in the grating plane. When the system is used as a position finding instrument, the presence of an object in the particular object plane may be determined.

Figure 6:
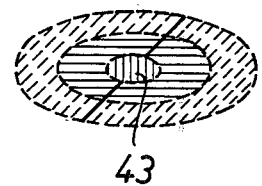
FIG. 6 shows a further embodiment of pupil subdivision.

FIG. 6 shows an arrangement similar to that of FIG. 4, but annular. The central part 43 is made disk-like.

FIG. 7 again shows schematically an arrangement of FIG. 1 for the purpose of explaining the derivation, the processing and the time function of the measuring signals. The case illustrated is one of light bundles passing through diametral sections A and A' of objective 1 focusing in the plane of prismatic grating 2. An oscillatory or constant motion drive 7 acting transversely to the optic axis is provided for the prismatic grating 2 forming one side of the condensing lens 3. Two sets of photoelectric receiver pairs 5g, 5g' and 5r, 5r' associated with the diametral sections A, A' are mounted in the exit pupil 3' of focusing system, 1, 2, 3. For the focus setting shown, a relative motion between grating 2 and object image causes AC output signals across receivers 5r', 5g', and push-pull signals across 5r, 5g, and in-phase signals across 5r, 5r' and 5g, 5g', as shown by the curves at the receiver outputs. Accordingly, the outputs of receivers 5r' and 5g', furthermore 5r and 5g each are provided with a push-pull amplifier 9', 9'', the DC signal components being simultaneously eliminated.

If now the image focus plane lies in front of, or to the rear of grating 2, then corresponding to the parallaxes of objective sections A, A', the phase of the signal at amplifier 9'' arising from section A is shifted in one direction and the phase of the signal arising from section A' will be shifted in the other. These phase shifts allow the determination of the magnitude and the sign of the offset from focus.

Besides this focus offset, magnitude of the phase shift will also depend on the aperture or on the distance from section A, A' of the objective to the axis. If corresponding to a finer subdivision of objective 1, a larger number of photoelectric receivers with corresponding push-pull amplifiers is used, then one obtains a correspondingly finer phase gradation at the output signals of the amplifiers. FIGS. 7a, 7b and 7c show the continous gradation of phase $\phi$ of the brightness along pupil aperture A, when the focus plane is in front or behind grating 2 in two symmetric exit pupils. When there is focusing, as in FIG. 7b, there will be the same phase in any pupil section. It will be noted that the phase changes near the axis vanish, i.e., they are unsuitable for distance measurements. If the position of the focus plane is altered in either direction, no phase changes occur in the central pupil section, because there are no changes in perspective image position.

As the pupil section increasingly lies farther off the optic axis, perspective image changes arise, which will be noticeable on account of the above-mentioned increasing phase shifts. If the pupil sections are symmetric with respect to the axis, the degree of phase shift is always the same and of opposite sign. The phase shift signs invert for symmetric positions of focus and grating planes.

Figure 8:
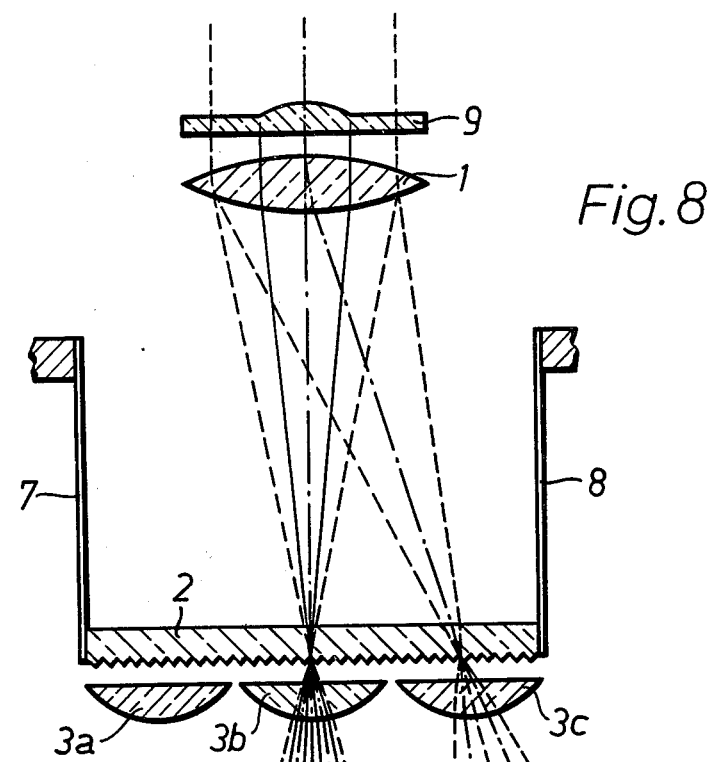
FIG. 8 shows a device for determining the distances of objects at different locations.
Figure 9:
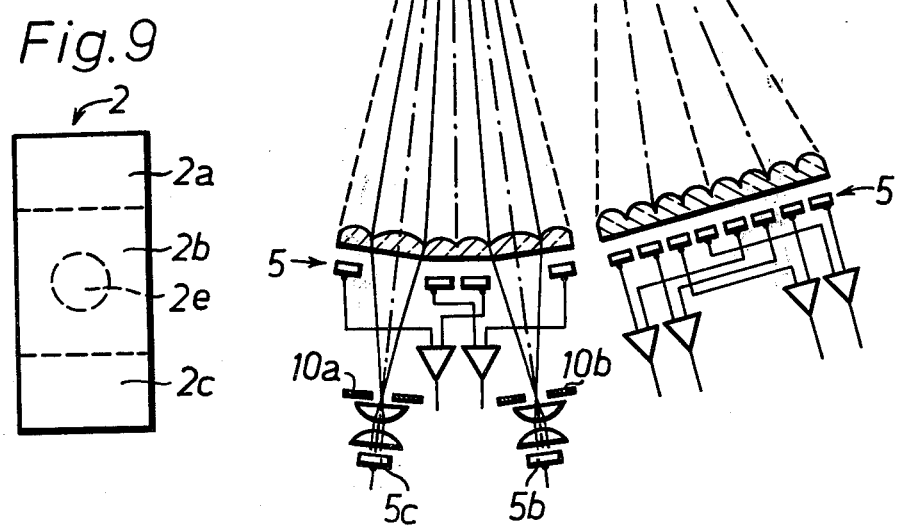
FIG. 9 shows image subdivision in the screen-grid plane.

FIGS. 8 and 9 show an arrangement in schematic form, wherein field lenses 3a, 3b and 3c apart from the grating 2 plane are associated with the various image sections 2a, 2b and 2c. On account of the design a zone plate 9 in front of objective 1, an object distance Y corresponds to image section 2b (FIG. 9), and an object distance X to a partial section 2e located in 2b. By means of a subsequent focusing of partial section 2e near, but not on stops 10a and 10b, the focusing signal related to 2e is so selected that no part of the remaining field 2b for the Y distance measurement is covered up. The light fluxes from partial section 2e are converted into electrical signals by means of subsequent photoelectric receivers 5c and 5d.

Figure 7:
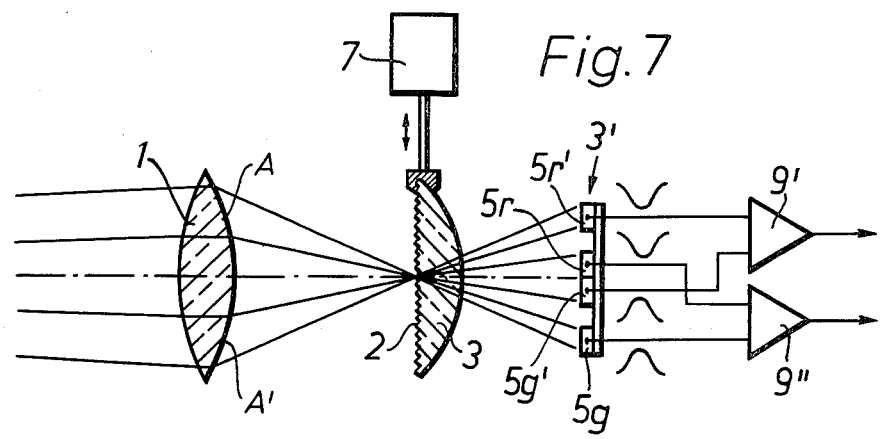
FIG. 7 shows the arrangement of FIG. 1 in schematic form.
Figures 7A, 7B, 7C:
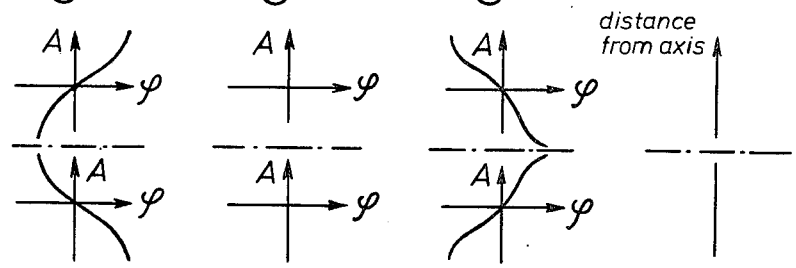
FIGS. 7a, 7b, 7c show the phase variations along the pupil aperture.

FIGS. 10 through 13 illustrate various analysis procedures concerning for instance the output signals of push-pull amplifiers 9', 9'' of FIG. 7.

Figure 10:
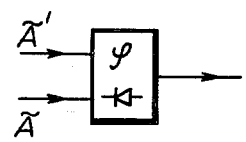
FIGS. 10–13 show signal analysis circuits.

In FIG. 10, signals $\widetilde{A}$, $\widetilde{A}'$ from pupil sections A, A' following their being made out-of-phase are fed to a single phase-sensitive rectifier 20 lacking a reference signal from the grating motion. The amplitude of the output signals provides a very precise criterion of focus, without however providing sign information.

Figure 11:
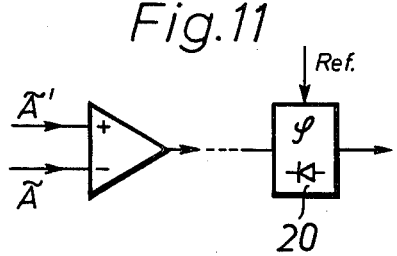

As shown by FIG. 11, the two signals $\widetilde{A}$, $\widetilde{A}'$ first are subtracted from one another, thereby already providing a very accurate focus criterion, however lacking sign information, on account of a null transition of the amplitude difference when there is the same phase. Subsequent phase-sensitive rectification of this differential signal with reference to the drive signal of grating 2 provides the sign of the offset.

Figure 12:
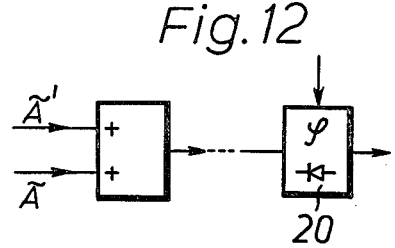

As shown by FIG. 12, both signals $\widetilde{A}$, $\widetilde{A}'$ first are summed in order to ascertain any angular motions of the object being measured or to display the object catchment range by means of a signal maximum of the sum. The sign of angular motion is obtained from subsequent phase-sensitive rectifcation of the sum signal with reference to the grating drive signal.

Figure 13:
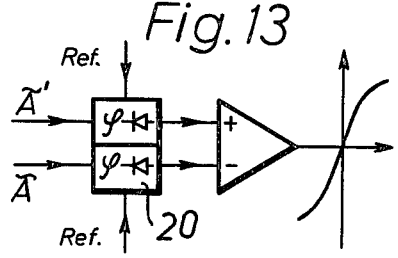

Lastly, as shown in FIG. 13, both signals $\widetilde{A}$, $\widetilde{A}'$ are separately fed each to one phase-sensitive rectifier 20, together with a reference signal from grating drive 7, and the resulting DC potentials are analyzed as differences and sums in order to determine the motion of the object.

Obviously, the analysis methods of FIGS. 10 through 13 may be combined arbitrarily.

The electrical signals which are indicative of the position, velocity and direction of object displacement are applied to suitable indicator means. Alternatively, or additionally such signals may be applied to displacement means to adjust the focusing of the optical imaging system. Such displacement means may be arranged in a servo-loop to provide a follow-up facility.

FIGS. 14a and 14b show a system comprising optic correlators as proposed for guiding blind persons. FIG. 14a is a front view, and FIG. 14b is a lengthwise section. The system is provided with a forward directed objective 1 focusing forward objects on grid 2 of a first optical correlator and with a second objective 1a directed downward, focusing steps or slopes on the grid of a second optical correlator, and thus sensing such objects. The second correlator comprises also a downwardly directed illumination device or bulb 16 permitting use of the system in darkness. A set of finger sensors 14a, 14b, 14c, 14e, 14f, 14g is associated with each correlator, each sensor within a set being related to the various distances of the objects. These sensors are controlled by electronic circuits shown in block form as 11a, 11b, 11c, 11e, 11f, 11g, which in turn are controlled by signals from the correlators.

These sensors are controlled by corresponding signals, for instance by magneto strictive or piezoelectric oscillators 11a, 11b, 11c, 11e, 11f, 11g resonating strip springs acting on the sensors. Such an arrangement is shown in detail for oscillator 11a acting on spring 12a driving sensor 14a. A thumb switch is used to turn the apparatus on. Key 14a is to be used by the little finger, 14b by the ring finger, 14c by the middle finger, and 14e by the index finger. These fingers being staggered in height for the sequence just mentioned, one obtains a meaningful height relation of the appropriate fields 2a, 2b, and 2c, which were described with respect to position and determination already in connection with FIGS. 8 and 9. Vibrator 14e is associated with the index figer, said vibrator corresponding to the optical "pointer field" 2e.

FIG. 15 shows an arrangement wherein four aperture sections of the entrace objective 1 are especially characterized and referenced as $1'$, $1'''$, $1^{IV}$, $1^V$. A pyramid grating 12, shown in detail in FIG. 15a, is mounted behind a beam deflector in the rear of objective 1 and fundamental edges of the pyramid grating run parallel to the dashed lines connecting the opposite aperture sections. Such as gable roof-like grating is disclosed in British Pat. No. 1,249,302. The oscillators used in the devices of the foregoing figures, causing alternating light impingement of the gratings for detecting the direction of the object movement, are replaced by a wobble plate 11 acting as beam deflector inducing light flux motion with respect to the pyramid grating 12 and thus applying regular and periodic alternations of the light fluxes to the pupil images. For the sake of clarity, its rotational drive is omitted from the Figure. A field lens 3 behind pyramid grating 12 in conjunction with the refraction of said grating focuses the entrance pupil of objective 1 as four separately located pupil images 4a, 4b, 4c, 4d, each of these images comprising aperture section projections $4a'$, $4a'''$, $4b'$, $4b'''$, $4c^V$, $4c^{IV}$, $4d^V$, $4d^{IV}$ corresponding to the aperture sections of objective 1. Simultaneously there is splitting of the image by means of the four flank or side groups of the grating, so that pupil images 4a, 4b or 4c, 4d arise from light fluxes having traversed different grating flank groups. The result is complementarity between pupil image 4a or 4c with pupil image 4b or 4d with respect to the generating light fluxes. The position of the focused object structure relative to the flanks of grating 12 also is significant for the illumination of pupil images 4a, 4b or 4c, 4d, whereas the difference in parallax (solid angle) of different object regions is significant for the illumination of pupil sections $4a'$ through $4d^{IV}$. It is observed that the light flux through the central aperture section $1''$ of the objective is not used in this arrangement. The photoelectric receivers associated with the pupil image sections are connected as shown in pairs to push-pull amplifiers, from the four output signals of which the sign and the magnitude of the offset or the motion of the object being measured in three coordinates is then determined as already described above.

These output signals being displaced in phase relative to one another by the different spatial arrangement of the photoelectric receivers generating these signals constitute rotating field signals known per se from the Journal of Research of the National Bureau of Standards - C. Engineering and Instrumentation, Vol. 65 C, No. b 2, April June 1961- "An Automatic Fringe Counting Interferometer for Use in the Calibration of Line Scales."

Figure 16:
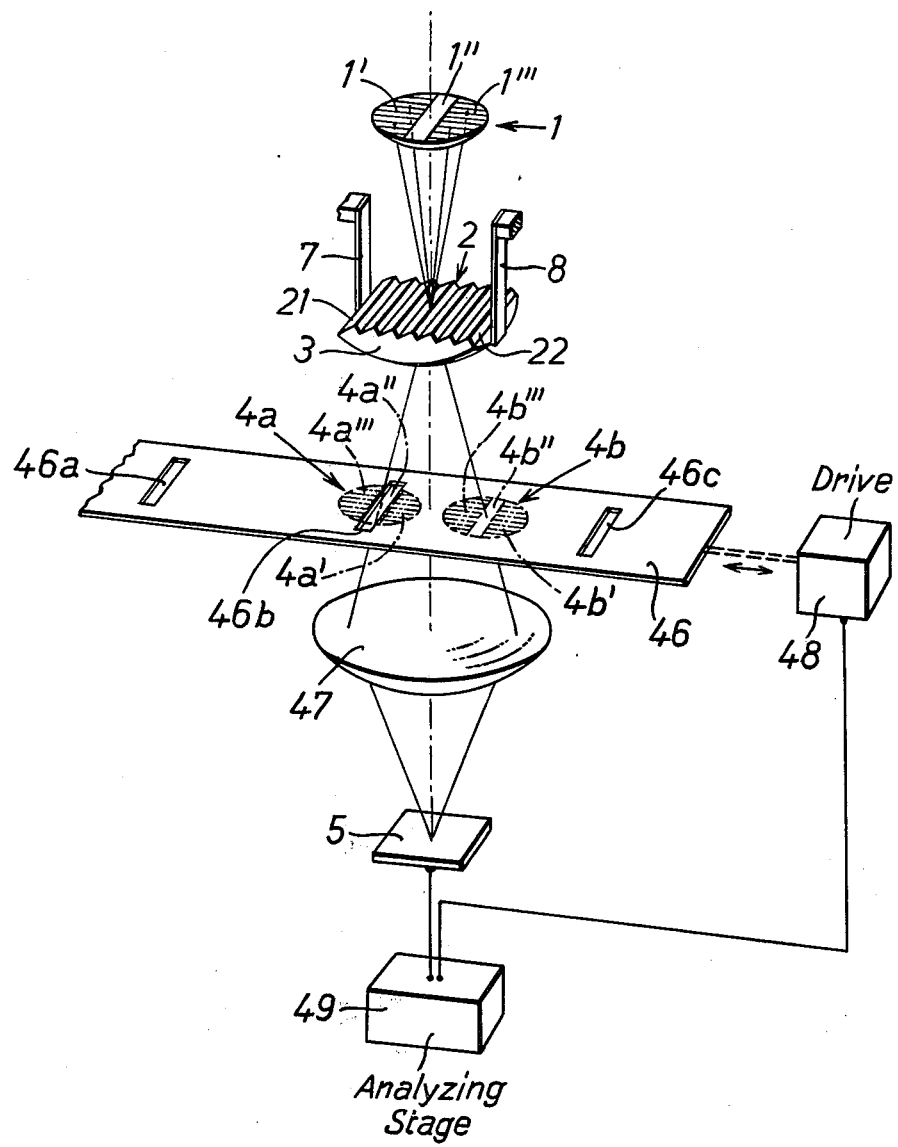

The schematic arrangement shown in FIG. 16 differs from the one shown in FIG. 1 by utilizing a common photoelectric receiver 5 for the generation of electrical signals from light fluxes emitted by the pupil images 4a and 4b.

For the purpose of the successive direction of these light fluxes to the photoelectric receiver 5, a chopper or movable aperture 46, known per se by apparatus used in photometry and disclosed for instance in U.S. Pat. Nos. 3,457,412 and 3,255,255, is provided in the plane of the pupil images.

Slots 46a, 46b, 46c spaced at intervals larger than the distance between the pupil images are applied and the chopper or movable aperture is driven by a drive unit 48 in the direction of the arrow.

It is evident from this arrangement that light fluxes emitting from the pupil images ranges $4a' - 4a'''$ and $4b'$ to $4b'''$ respectively will arrive via a condensing lens 47 the photoelectric receiver 5 only if they are set free by one of the slots 46a to 46c.

The electrical signals generated by the photoelectric receiver 5 on behalf of the impingement with the light fluxes are processed in an analyzing stage 49 which is additionally connected with the drive unit 48, pulses of which control the supply of the electrical signals to adequate channels.

We claim:

1. In a method for determining the position of a focusing plane of an image within an optical device including an optical imaging system, the improvement comprising the steps of defining the entrance pupil of said optical imaging system into a plurality of different regions ($1'$; $1'''$; $1^{IV}$; $1^V$); imaging via said optical imaging system at least one object to be measured which is emitting light fluxes traversing said regions as a set of light fluxes on at least one spatial frequency filter (2; 12) of an optical image correlator;

jointly modulating said set of light fluxes by means of said spatial frequency filter;

splitting said set of light fluxes corresponding to the respective pupil regions into a pair of sets of partial light fluxes;

applying each of said partial light fluxes to photoelectric receiving means (5c, 5d; 5g'; 5r; 5r') for generating electrical output signals corresponding to said partial light fluxes; and processing said signals to derive further electrical signals being indicative of positions of the focusing plane.

2. A method as claimed in claim 1, comprising further the step of feeding said further electrical signals to indicator means for indicating the distance between the object and said imaging system.

3. The method of claim 1, wherein individual ones of said set of partial light fluxes are successively applied to a common photoelectric receiving means.

4. The method of claim 1, wherein individual ones of said set of partial light fluxes are successively applied to separate photoelectric receiving means.

5. The method of claim 1, wherein individual ones of said set of partial light fluxes are simultaneously applied to separate photoelectric receiving means.

6. The method of claim 1, wherein respective light fluxes are geometrically split in correspondence with respective ones of said pupil regions traversed by said light fluxes.

7. The method of claim 1, wherein respective light fluxes are physically split in correspondence with respective ones of said pupil regions traversed by said light fluxes.

8. The method of claim 1, comprising yet further the step of applying said further electrical signals to displacement means to adjust the focusing of the optical imaging system.

9. The method of claim 1, wherein said sets of each of said pairs are disposed in antiphase relationship, and each of the respective pairs of said sets of light fluxes is applied successively to a common pair of photoelectric receivers (5c, 5d), output signals derived from each pair of receivers associated with a respective pupil region (1, 1') are applied to a respective push-pull amplifier (9', 9''), and output signals derived from such amplifiers are compared with one another to provide an indication of the sign of any relative displacement between the image and the spatial frequency filter (2, 12).

10. The method of claim 9, wherein the magnitudes of said output signals of said push-pull amplifiers are compared to provide an indication of the sign of any relative displacement between the image and the spatial frequency filter.

11. The method of claim 9, wherein the frequencies of said output signals of said push-pull amplifiers are compared to provide an indication of the sign of any relative displacement between the image and the spatial frequency filter.

12. The method of claim 9, wherein the phase relationships of said output signals of said push-pull amplifiers are compared to provide an indication of the sign of any relative displacement between the image and the spatial frequency filter.

13. The method of claim 1, wherein said sets of each of said pairs are disposed in antiphase relationship, and each of the respective pairs of said sets of light fluxes is applied simultaneously to separate pairs of photoelectric receivers, output signals derived from each pair of receivers associated with a respective pupil region are applied to a respective push-pull amplifier, and output signals derived from such amplifiers are compared with one another to provide an indication of the sign of any relative displacement between the image and the spatial frequency filter.

14. The method of claim 13, wherein the magnitudes of said output signals of said push-pull amplifiers are compared to provide an indication of the sign of any relative displacement between the image and the spatial frequency filter.

15. The method of claim 13, wherein the frequencies of said output signals of said push-pull amplifiers are compared to provide an indication of the sign of any relative displacement between the image and the spatial frequency filter.

16. The method of claim 13, wherein the phase relationships of said output signals of said push-pull amplifiers are compared to provide an indication of the sign of any relative displacement between the image and the spatial frequency filter.

17. The method of claim 1, wherein light fluxes traversing only respective outer edge portions (41, 45) of the pupil of the optical system are utilized.

18. The method of claim 1, comprising the step of determining the angular velocity of the object by comparing the frequencies of electrical signals derived from said photoelectric receiver means, in response to light fluxes traversing a central portion (43) of said pupil of said imaging system.

19. The method of claim 1, comprising the step of determining the angular velocity of the object by comparing the phase relationship of electrical signals derived from said photoelectric receiver means, in response to light fluxes traversing a control portion (43) of said pupil of said imaging system.

20. The method of claim 1, wherein the determination of the angular velocity of said object is executed by comparing the frequencies of electrical signal components derived from photoelectric receiver means and corresponding to different regions of said pupil of said imaging system.

21. The method of claim 1, wherein the determination of the angular velocity of said object is executed by comparing the phase relationship of electrical signal components derived from photoelectric receiver means and corresponding to different regions of said pupil of said imaging system.

22. The method of claim 1, wherein the relative magnitude of said further electrical signals is determined to receive in said indicator means an indication of the distance between said object and said imaging system with the proper arithmetic sign.

23. The method of claim 1, wherein a relative movement between said spatial frequency filter and said image of said object is additionally generated to ascertain from the phase relationship of the electrical signals obtained from said relative movement the proper arithmetic sign of said indication.

24. The method of claim 1, wherein a relative movement between said spatial frequency filter and said image of said object is additionally generated to ascertain from the frequencies of the electrical signals obtained from said relative movement the proper arithmetic sign of said indication.

25. The method of claim 1, wherein the relative magnitude of said further electrical signals is determined to receive in said displacement means an adjustment of the distance between said object and said imaging system with the proper arithmetic sign.

26. The method of claim 1, wherein a relative movement between said spatial frequency filter and said image of said object is additionally generated to ascertain from the phase relationship of the electrical signals obtained from said relative movement an adjustment of said displacement means with the proper arithmetic sign.

27. The method of claim 1, wherein a relative movement between said spatial frequency filter and said image of said object is additionally generated to ascertain from the frequencies of the electrical signals obtained from said relative movement an adjustment of said displacement means with proper arithmetic sign.

28. The method of claim 1, wherein respective light fluxes are additionally modulated.

29. In an apparatus for determining the position of a focusing plane of an image within an optical device comprising an optical image correlator incorporating at least one spatial frequency filter, an optical imaging system to image an object to be measured on said spatial frequency filter, and photoelectrical receiving means, the improvement comprising means for defining the entrance pupil of said imaging system into a plurality of different regions being traversed by light fluxes emitted from said object to be measured as a set of light fluxes and used for imaging said object on said spatial frequency filter which jointly modulates said set of light fluxes; means for splitting said set of light fluxes corresponding to the respective pupil regions into a pair of sets of partial light fluxes; said photoelectric receiving means for generating electrical output signals in response to respective ones of said partial light fluxes; and means for processing said signals to derive further electrical signals being indicative of the position of said focusing plane of said image.

30. The apparatus as claimed in claim 29, wherein the spatial frequency filter comprises linear optical grating means (2) having beam splitting properties, the grating forming at least two non-overlapping images (4a, 4b) of the entrance pupil of the optical system via condenser means (3), the photoelectric receivers (5g, 5', 5r, 5r') to provide a pair of electrical signals associated with each of said images, respective ones of said electrical signals of each pair being in phase opposition to one another.

31. Apparatus as claimed in claim 29, comprising a light stop (2') to mask the photoelectrical receiver means against light flux traversing a central portion of the pupil of the optical system.

32. Apparatus as claimed in claim 29, wherein said optical system comprises a lens having respective lens zones (41, 42, 43, 44, 45) of mutually different focal lengths associated with respective ones of said different pupil regions, said respective lens zones producing sharp object images on said spatial frequency filter (2) corresponding to objects at respectively different distances from the lens (1), of said image system, the photoelectric means comprising at least one photoelectric receiver associated with each of said different pupil regions.

33. Apparatus as claimed in claim 32, wherein a non-visual indicator device (14a, 14b, 14c, 14e, 14f, 14g) is provided for each object to lens distance to adapt said apparatus to provide an aid for the blind.

34. Apparatus as claimed in claim 29, wherein said optical system comprises a lens having respective lens zones of mutually different focal lengths associated with respective lens zones producing sharp object images (2a, 2b, 2c, 2e) on said spatial frequency filter (2) corresponding to different sections of the object, said photoelectric means comprising at least one pair of photoelectric receivers associated with each of said different pupil regions.

35. Apparatus as claimed in claim 34, wherein each of said different pupil regions is substantially annular.

36. Apparatus as claimed in claim 34, wherein each of said different pupil regions comprises an elongate strip portion of the pupil.

37. Apparatus as claimed in claim 29, comprising at least one phase-sensitive rectifier (20), having input means to which electrical signals derived from two different pupil regions are applied.

38. Apparatus as claimed in claim 37, comprising at least two phase-sensitive rectifiers (20) and summing means connected to output means of said phase-sensitive rectifiers.

39. Apparatus as claimed in claim 29, comprising at least one differential amplifier having input means to which only respective electrical signals derived from each of two different pupil regions are applied.

40. Apparatus as claimed in claim 39, comprising a phase-sensitive rectifier (20), having first input means to which an electrical signal derived from said differential amplifier is applied, and having second input means to which an electrical signal derived from said drive means for said spatial frequency filter is applied as a reference signal.

41. Apparatus as claimed in claim 39, comprising a phase-sensitive detector (20) having first input means to which a sum signal formed from electrical signals derived from two photoelectric receivers respectively associated with two different pupil regions is applied, having second input means to which an electrical signal derived from said drive means for said spatial frequency filter is applied as a reference signal, and having input means connected to indicator means to indicate the position of the focusing plane of the object.

42. Apparatus as claimed in claim 39, comprising at least one phase-sensitive rectifier (20) and at least one differential amplifier, said rectifier having first input means to which said drive signal corresponding to relative movement between said image of said object and the spatial frequency filter is applied, and having second input means to which a respective signal derived from each of said different pupil regions is applied, the rectifier providing two output signals which are applied in respective input means of said differential amplifier, output signals derived from said differential amplifier being indicative of movement between said image of said object and said spatial frequency filter relative to three mutually perpendicular directions.

43. Apparatus as claimed in claim 29, wherein a pair of said photoelectric receivers ($5g$, $5g'$, $5r$, $5r'$) is associated with each respective one of said pupil regions (A, A'), one photoelectric receiver of each pair being connected to first input means of respective ones of two differential amplifiers ($9'$, $9''$), and the respective other photoelectric receiver of each pair being connected to second input means of respective ones of the two differential amplifiers.

44. Apparatus as claimed in claim 29, wherein said spatial frequency comprises a pyramidal optical grating (12) having beam splitting properties and forming, according to the number of the pyramidal surfaces, a plurality of non-overlapping images ($4a$; $4b$; $4c$; $4d$) of said entrance pupil of said optical imaging system via condenser means (3), said photoelectric receiver means generating from light fluxes emitting from said images electrical signals being displaced in phase relative to one another, thus constituting rotating field signals.

45. Apparatus as claimed in claim 29, comprising means (7;11) for an additional modulation of said light fluxes.

46. Apparatus as claimed in claim 45, comprising a wobble plate (11) causing an additional modulation of said light fluxes by circulatory beam deflection.

47. Apparatus as claimed in claim 45, comprising drive means (7) to provide relative displacement between said image of the object and said spatial frequency filter (2).

* * * * *